United States Patent [19]

Yamamoto et al.

[11] Patent Number: 5,770,452

[45] Date of Patent: Jun. 23, 1998

[54] QUANTITATIVE DETERMINATION OF LIPID, AND OF CO-EXISTING TWO COMPOUNDS

[75] Inventors: Nobuko Yamamoto, Isehara; Yasuko Tomida, Atsugi; Junji Ohyama, Yamato; Tsuyoshi Nomoto; Masahiro Kawaguchi, both of Atsugi, all of Japan

[73] Assignee: Canon Kabushiki Kaisha, Tokyo, Japan

[21] Appl. No.: 458,258

[22] Filed: Jun. 2, 1995

Related U.S. Application Data

[62] Division of Ser. No. 942,417, Sep. 9, 1992, Pat. No. 5,491,093.

[30] Foreign Application Priority Data

| Sep. 9, 1991 | [JP] | Japan | 3-228960 |
| Sep. 9, 1991 | [JP] | Japan | 3-228961 |
| Sep. 11, 1991 | [JP] | Japan | 3-231914 |

[51] Int. Cl.$^6$ ............................................. G01N 21/00
[52] U.S. Cl. ........................ 436/86; 436/8; 436/13; 436/15; 436/71; 436/164
[58] Field of Search ........................ 436/8, 13, 15, 436/71, 86, 164

[56] References Cited

U.S. PATENT DOCUMENTS

| 4,104,030 | 8/1978 | Hopkins, II et al. | 23/230 B |
| 4,219,337 | 8/1980 | Grossberg et al. | 23/230 B |
| 4,369,250 | 1/1983 | Gindler | 435/18 |
| 4,485,176 | 11/1984 | Bollin, Jr. et al. | 436/86 |
| 4,579,825 | 4/1986 | Seidel et al. | 436/175 |
| 4,608,347 | 8/1986 | Bernstam | 436/8 |
| 4,786,605 | 11/1988 | Mauck et al. | 436/86 |
| 4,816,411 | 3/1989 | Yun et al. | 436/13 |
| 4,820,628 | 4/1989 | Weitz | 435/4 |
| 4,839,294 | 6/1989 | Almong et al. | 436/71 |
| 4,883,765 | 11/1989 | Tamir et al. | 436/71 |
| 4,960,710 | 10/1990 | Lau | 436/86 |
| 4,980,295 | 12/1990 | Udy | 436/71 |
| 5,041,224 | 8/1991 | Ohyama et al. | 210/500.27 |
| 5,183,879 | 2/1993 | Yuasa et al. | 528/503 |
| 5,246,864 | 9/1993 | Purdie | 436/71 |
| 5,300,440 | 4/1994 | Alan | 436/86 |
| 5,348,889 | 9/1994 | Terashima et al. | 436/8 |

FOREIGN PATENT DOCUMENTS

| 0296136 | 12/1988 | European Pat. Off. | G01N 33/543 |
| 0407035 | 1/1991 | European Pat. Off. | G01N 33/92 |
| 272927 | 10/1989 | German Dem. Rep. | |
| 2050666 | 5/1987 | Japan. | |
| 2-59075 | 2/1990 | Japan | B05D 7/24 |
| 2043244 | 10/1980 | United Kingdom | G01N 21/75 |

OTHER PUBLICATIONS

Brewer "Solving Problems in Analytical Chemistry", 1980, pp. 261, 272, 276–285.

The Journal of Biological Chemistry, vol. 193, 1951, pp. 265–275, Lowry et al., "Protein Measurement With the Folin Phenol Reagent".

(List continued on next page.)

*Primary Examiner*—Jill Warden
*Assistant Examiner*—Sharidan Carrillo
*Attorney, Agent, or Firm*—Fitzpatrick, Cella, Harper & Scinto

[57] ABSTRACT

Lipid is determined quantitatively by treating a sample with a surfactant in an aqueous medium to obtain a liquid sample dispersion, then reacting the dispersion with a reagent containing cupric ion and bicinchoninic acid, and measuring a colored state developed by complex formation of bicinchoninic acid with cuprous ion formed from cupric ion in the presence of lipid. This method can be effectively applied to determination of amphiphilic lipid having a tendency of gathering in an aqueous medium. Further, two different species interfering with each other in quantitative determination thereof are determined respectively by conducting two different determination methods on the same sample followed by calculation using the values obtained.

8 Claims, 2 Drawing Sheets

OTHER PUBLICATIONS

Biochimica et Biophysica Acta, Biomembranes, vol. 821, No. 3, Dec. 19, 1985, pp. 470–478, Lichtenberg, "Characterization of the Solubilization of Lipid Bilayers by Surfactants".

Analytical Biochemistry, vol. 150, No. 1, pp. 76–85, Oct. 1985, P.K. Smith et al., "Measurement of Protein Using Bicinchoninic Acid".

Hoeflmayr, J. and Fried, R; Med. und Ern., 7, 9–10 (1966).

The Journal of Biological Chemistry, vol. 193, pp. 265–275, O.H. Lowry et al., "Protein Measurement With The Folin Phenol Reagent".

Proceedings Of The National Academy Of Sciences, vol. 77, No. 1, pp. 323–327, Jan. 1980, Kuo–Sen Huang, et al., "Delipidation of Bacteriorhodopsin and Reconstitution With Exogenous Phospholipid".

Methods in Enzymology, vol. 31, pp. 667–678, D. Oesterhelt, et al., "Isolation of the Cell Membrane of *Halobacterium halobium* and Its Fractionation into Red and Purple Membrane".

Clinica Chimica Acta, vol. 79, pp. 93–98, 1979, M. Takayama, et al. "A New Enzymatic Method For Determination Of Serum Choline–Containing Phospholipids".

Riemenschneider et al., "Determination of Fatty Acids in Small Amounts of Plasma and in Lipid Components of Tissues by Ultraviolet Spectroscopy".

The American Journal of Clinical Nutrition, vol. 6, No. 6, 1958.

Smith, et al., *Meas. of protein using bicinchoninic acid*, Analytical Biochemistry, vol. 150 (1985), pp. 76–85.

Lichtenberg, *Char. of the Solub. of Lipid Bilay. by Surf.*, Biochimica et Biophysica Acta, vol. 821, No. 3 (Dec. 1985), pp. 470–478.

Takayama, et al., Clinica Chimica Acta, vol. 79 (1977), pp. 93–98.

Lowry, et al., The Journal of Biological Chemistry, vol. 193 (1951), pp. 265–275.

Huang, et al., Proceedings of the National Academy of Sciences, vol. 77, No. 1 (Jan. 1980), pp. 323–327.

QUANTITATIVE DETERMINATION OF LIPID, AND OF CO-EXISTING TWO COMPOUNDS

This application is a division of application Ser. No. 07/942,417 filed Sep. 9, 1992 now U.S. Pat. No. 5,491,093.

BACKGROUND OF THE INVENTION

1. Field of the Invention

The present invention relates to a method of quantitative determination of lipid. Further, the present invention relates to a simple method of quantitative determination of each of two components such as lipid and protein coexisting in a system without separating the components.

2. Related Background Art

Lipids are construction components of cells or organisms. Among the lipids, phospholipid is a principal lipid in construction of various membranes in the cells, such as plasma membrane, nuclear membrane, endoplasmic reticulum membrane, mitochondrial membrane, Golgi body membrane, lysosome membrane, and the like. The phospholipid is an amphiphilic molecule having both a polar group and a hydrophobic group in the molecule. When phospholipid is suspended in water, the polar groups become hydrated with water molecules, and the hydrophobic groups are excluded from the aqueous environment to cause gathering of the hydrophobic groups of the lipids. Consequently, micelles, lipid bilayers having a bimolecular membrane structure, or hexagonal II structures are formed: the state of gathering depending on the balance of the volumes of the hydrated hydrophilic groups and the hydrophobic groups. Among such structures, the lipid bilayer is the basic structure of biomembranes. The bilayer of phospholipid forms a closed vesicle (liposome), which is capable of incorporating membrane protein or the like as a constituent thereof and enclosing an aqueous phase therein. Therefore, the phospholipid bilayer structure is frequently employed as a model of a biomembrane for substance permeation, information transmission, and so forth. Further, the liposome is promising for use for a medicine capsule since the liposome is capable of retaining a water-soluble substance in its internal aqueous phase.

Many methods are known for quantitative determination of phospholipid, including a wet combustion method (Hoeflmayr, J. and Fried, R; Med. und Ern., 7, 9–10 (1966)) and a choline oxidase-phenol method (Takayama, M., Itoh, S., Nagasaki, T. and Tanimizu, I., Clin. Chim. Acta 79 93–98 (1977)). In the wet combustion method, the phospholipid is determined by adding sulfuric acid and a permanganate salt to a sample; heating the mixture in a boiling water bath to liberate the constituting phosphoric acid; adding ammonium molybdate and a reducing agent thereto; and measuring light absorbance caused by molybdenum blue formed thereby. In the choline oxidase-phenol method, the phospholipid is determined by reacting phospholipase D with the phospholipid in a sample to liberate the constituting choline; further reacting choline oxidase with the resulting choline to form betaine and hydrogen peroxide; and measuring light absorbance of the product of a quantitative condensation oxidation of phenol with 4-amino-antipyrine caused by hydrogen peroxide in the presence of peroxidase.

The above-mentioned wet combustion method has disadvantages of being troublesome in the operation of sequential addition of several reagents, and danger of bumping and measurement error by evaporation owing to heating in the presence of sulfuric acid in a boiling water bath. The choline oxidase-phenol method has disadvantages of instability of the enzyme, need for storing the reagents in a cold and dark condition, and insufficiency of reproducibility of measurement data obtained during lapse of time.

Generally, absorption spectrochemical quantitative analysis, in which the absorbance is measured at an absorption wavelength characteristic of the object of analysis in the sample, is widely used practically in quantitative determination of a substance because of simplicity of operation of direct measurement of absorbance, and needlessness of reacting the analysis object with another substance thus enabling the use of the sample later for another use.

However, this method of analysis has not been employed in the determination of lipids, because lipids such as phospholipid constituted of amphiphilic molecules form in an aqueous medium an aggregate in various state which scatters light and prevents precise assay of lipid concentration by light absorbance.

The constitution components of living matter such as lipids, proteins, nucleic acids, sugars are frequently handled in a coexisting state. Therefore, quantitative determination of such coexisting substances is an important operation.

Biomembranes have in a structure of a bilayered membrane are mainly constituted of lipid molecules, and protein gathers therein by non-covalent bonds, thereby functioning as a barrier for maintaining the interior medium. The ratio of lipid to protein in biomembranes differs greatly depending on the respective membranes. In mitochondrial membranes, for example, protein is contained 4 times as much as lipid. On the contrary, in some biomembranes, lipid is contained in an amount several times as much as protein. Accordingly, the ratio of lipid to protein in biomembrane in respective organs is an important object of study.

Various biomembrane models in which lipid and protein are coexisting are widely used in the study of the structure and the function of the biomembranes. The examples include proteoliposome which has closed vesicles constituted of artificial bimolecular lipid membrane containing therein protein; fine particles of glass beads or a high polymer which have lipid or protein adsorbed on the surface thereof; a planar lipid membrane formed in a small hole in a substrate made of TEFLON (tetrafluoroethylene fluoro carbon polymer) or the like (a black lipid membrane), or a planar bimolecular film reconstructed by sticking or patch-pipeting into which protein is incorporated; and Langmuir-Blodgett built-up films (LB built-up films) in which a lipid-protein coexisting system is built up in layers in a molecular level. In these artificial films also, the determination of the lipid and the protein is important in evaluating the function thereof.

If the optimum ratio of lipid to protein in natural, or artificially synthesized membrane structures can be obtained by quantitative determination, and a membrane can be synthesized effectively according to the derived ratio, then various membrane structure can be industrially synthesized at low cost without wasting valuable protein.

Further examples of lipid-protein coexisting systems include liposome, i.e., a closed vesicle composed of phospholipid membrane, in which a functional protein such as water-soluble enzyme is enclosed; and emulsions in which lipid and protein are simply mixed in a liquid medium.

Heretofore, in the determination of lipid and protein in a coexisting system, the determination of lipid is affected by the presence of protein, and the determination of protein is affected by the presence of lipid. Therefore, lipid and protein could not be precisely determined in a coexisting state. In determination of lipid by the above-mentioned absorbance measurement, the influence of the absorbance of coexisting protein is not negligible.

Various methods for determining protein are known, including colorimetry utilizing a metal ion, UV absorption method based on tyrosine and triptophan, and UV absorption method based on peptide bonds. A typical method of the colorimetry is a Lowery method (J. Biol. Chim., vol. 193, p265 (1951)) employing a phenol reagent. This method utilizes a blue color developed by reaction of a phenol with protein. The main component of the reagent is phosphomolybdate or phosphotungstate, a complicated complex formed from the metal oxide and phosphoric acid. This complex reacts with a reducing agent such as protein to develop blue color of phosphomolybdate blue or phosphotungstate blue. The protein is determined by measurement of the absorbance caused by the color. In a color reaction method called a BCA method, protein present converts a cupric ion into a cuprous ion in an alkaline medium, and the cuprous ion forms a purple complex compound with bicinchoninic acid molecule (i.e., BCA: 4,4'-dicarboxy-2,2'-biquinoline). The protein is determined according to the absorbance of this complex compound.

On the contrary, the UV absorption method for determining protein includes measurement of absorption at 280 nm caused by tyrosine or triptophan, and measurement of absorption at 215 to 225 nm caused by the peptide linkage. The both measurement methods are advantageous in that the operation is simple and the sample is not lost in comparison with color development methods, but are disadvantageous in that the measurement of protein is based on the content of tyrosine or triptophan and the determination result varies greatly depending on the kinds of the protein and is susceptible to an interfering substance such as nucleic acid which has absorption in this absorption region.

In these known methods of determining protein, coexisting lipid also undergoes reaction to develop color. For example, in the Lowry method and other methods employing a phenol reagent, the phosphomolybdate is reduced by the protein to develop a blue color of phosphomolybdate blue, and simultaneously the coexisting lipid which exhibits reduction activity like the protein develops color similarly.

Accordingly, in the quantitative determination of each of lipid and protein coexisting in a system, they have to be separated before the determination of lipid and protein.

The separation is usually conducted by an extraction method in which the lipid component in the sample is dissolved in an organic solvent layer and is recovered as an organic solvent fraction, and the protein component insoluble in the organic solvent is recovered as an aqueous fraction. The obtained organic solvent fraction is concentrated and evaporated to dryness, and is quantitatively determined as the lipid fraction. The aqueous fraction containing the protein is concentrated and the protein therein is quantitatively determined by various methods.

Thus the conventional determination of lipid and protein coexisting in a system is extremely complicated.

In conventional methods, in spite of the complicated operations, the protein is liable to enter the organic solvent layer, and the lipid is liable to enter the aqueous layer in some proportions since the extraction with an organic solvent is based on equilibrated partition, which causes a determination error frequently. Moreover, loss of the sample is not negligible in the extraction process, so that a relatively large amount of a sample is required. Furthermore, in determination of lipid and protein contained in a membrane structure, strongly hydrophobic protein such as membrane protein may contaminate the organic solvent fraction in high probability, and the lipid and the protein may possibly exist in an unseparated state in the organic layer, which prevents precise quantitative determination.

The above discussion relates to a two component system containing lipid and protein. The same discussion may be made on a two-component system containing two components selected from lipids, sugars, nucleic acids, pigments and various medicines.

SUMMARY OF THE INVENTION

An object of the present invention is to provide a highly simplified method for determining, in an aqueous medium, lipid, particularly a simplified method for determining amphiphilic lipid which gathers in the aqueous conditions.

Another object of the present invention is to provide a simplified method for quantitatively determining each of two components such as lipid and protein coexisting in a two component system without separating the components, to solve the above-mentioned problems in determining the components in the two-component system.

According to an aspect of the present invention, there is provided a method for quantitative determination of lipid, comprising preparing a liquid sample dispersion by treating a sample with a surfactant in an aqueous medium, reacting the liquid sample dispersion with a reagent containing cupric ion and bicinchoninic acid, and measuring a colored state developed by complex formation of bicinchoninic acid with cuprous ion formed from cupric ion in the presence of lipid.

According to a further aspect of the present invention, there is provided a method of quantitatively determining a compound A and a compound B in an unknown sample containing the compound A and the compound B in a liquid medium, comprising determining the compound A by a determination method a to obtain a measured value Va and determining the compound B by a determination method b to obtain an measured value Vb, and deriving respective actual concentrations (x, and y) of the compound A and the compound B from the equations (I) and (II):

$$Va = x \cdot a_1 + y \cdot a_2 \quad (I)$$

$$Vb = x \cdot b_1 + y \cdot b_2 \quad (II)$$

where $a_1$ is a concentration constant of the compound A in the determination method a when the compound A exists alone in the liquid medium; $a_2$ is a concentration constant of the compound B in the determination method a when the compound B exists alone in the liquid medium; b1 is a concentration constant of the compound A in the determination method b when the compound A exists alone in the liquid medium; $b_2$ is a concentration constant of the compound B in the determination method b when the compound B exists alone in the liquid medium.

DESCRIPTION OF THE PREFERRED EMBODIMENT

Figure 1:
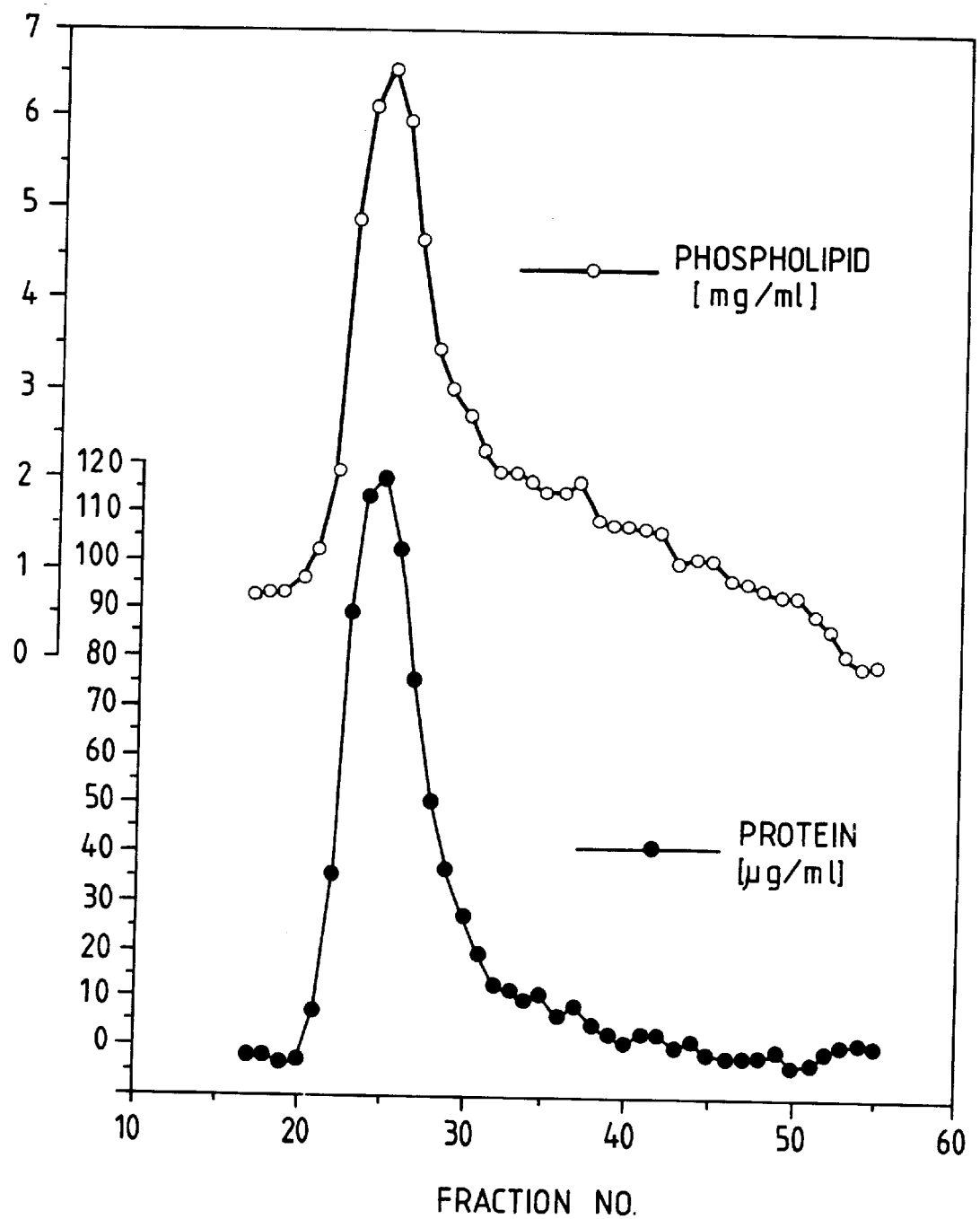
FIG. 1 illustrates a result of quantitative determination of coexisting phospholipid and protein according to the present invention.

Firstly, two methods of determining lipid in the present invention are described below.

In any of the lipid determination methods in the present invention, the lipid is treated with a surfactant to form a micelle composed of the lipid and the surfactant to enable the quantitative determination. For example, in the case of an amphiphilic lipid such as phospholipid, lipid aggregate formed in an aqueous medium is treated with a surfactant to form a micelle state composed of the lipid and the surfactant. The suitable treatment with a surfactant is a supersonic treatment or a water-bath heating treatment. One minute of supersonic treatment, or heating on a water bath at 60° C. for 10 minutes or longer is sufficient. An unknown sample and a standard sample should be treated in the same manner.

By such a treatment, the phospholipid with a surfactant is brought into a micelle state in correspondence with the lipid concentration regardless of the form of the aggregate such as liposome, a planar membrane, and a hexagonal II structure.

In a first method of quantitative determination of lipid, with a surfactant exhibiting no UV absorption in the measured UV range, the UV absorption is caused only by the lipid in a lipid-surfactant micelle state and the absorbance depends only on the concentration of the lipid, thus the lipid concentration being determined by measuring the UV absorbance. Any wavelength may be selected for the absorbance measurement within the range of from 230 to 290 nm if any substance other than lipid does not exist. However, if existence of other substance is anticipated, the wavelength needs to be selected at which the coexisting substance exhibits no or little absorbance. In research fields of handling or mimicking a biomembrane, the anticipated coexisting substance in most cases is protein. In this circumstance, the wavelength is preferably selected at around 240 nm, avoiding the maximum absorption of the protein of 280 nm.

Any surfactant may be used which exhibits no absorption in the UV region. The example of the useful surfactant includes octylglucoside (n-octyl-β-D-glucopyranoside), CHAPS (3-[(3-cholamidopropyl)dimethylammonio]-1-propanesulfonate, and HECAMEG (6-O-(N-heptylcarbamoyl)-methyl-α-D-glucopyranoside).

In a second method of quantitative determination of lipid, the lipid with a surfactant in a micelle state functions as a reducing agent to convert cupric ion into cuprous ion in an aqueous medium. The resulting cuprous ion forms with sodium salt of bicinchoninic acid (4,4'-dicarboxy-2,2'-biquinoline) a complex compound in purple color. Since this reaction proceeds quantitatively, lipid can be determined quantitatively by measurement of absorbance caused by the color of the complex compound.

The surfactant useful in this determination includes nonionic surfactants, and anionic surfactants, but are not particularly limited. The specific examples are Triton X-100, SDS (sodium dodecylsulfate), Briji 35, octylglucoside (n-octyl-β-D-glucopyranoside), CHAPS (3-[(3-cholamidopropyl)dimethylammonio]- 1-propane sulfonate), HECAMEG (6-O-(N-heptylcarbamoyl)-methyl-α-D-glucopyranoside), cholic acid, deoxycholic acid, and the like.

The color reaction of cupric ion with bicinchoninic acid is known also as a method of determination of protein by utilizing the reducing action of protein (Anal. Biochem., 150, p76 (1985)). This method is based on the principle that the cupric ion transforms into cuprous ion in the presence of protein in an alkaline medium, and the resulting cuprous ion forms a purple complex compound with the bicinchoninic acid molecule. The inventors of the present invention found that this reaction is sensitive not only to protein but also to lipid exhibiting similar reactivity, and completed the present invention on this finding.

Not all methods of quantitative determination of protein are applicable to quantitative determination of lipid. The present invention is characterized by the finding that the method for determining protein by use of bicinchoninic acid is applicable to quantitative determination of lipid. For example, the aforementioned Lowry method of protein determination, which utilizes reducing action of protein, may be expected to be useful for lipid determination by use of lipid exhibiting reducing action in place of protein. Actually, however, the sensitivity to lipid is as low as about 1/100 times that to protein. On the contrary, the sensitivity of the method of the present invention is only slightly lower than that to protein, about 1/3 times that to protein, being more sensitive than conventional quantitative lipid determination. Further this method is simple in operation. Therefore, the second method of determination of lipid of the present invention is highly practical when considered as a whole.

In the second method of the present invention, a liquid sample dispersion formed by treatment with a surfactant is reacted with a color reagent containing bicinchoninic acid and cupric ion, and the absorbance caused by the purple color developed by the presence of lipid is measured. The bicinchoninic acid and cupric ion are added in excess of the amount for reaction of the entire lipid in the sample. Usually, the final concentration of the bicinchoninic acid is about 1%, and that of cupric ion is from about 0.01 to 0.1%, and the sample dispersion is diluted so as to be measured in this reagent concentration. The reaction condition may be suitably selected. For example, heating treatment may be practiced at about 60° C. for about one hour, and cooled to room temperature, and the absorbance may be measured at a wavelength of, e.g., 526 nm. This method for determination of lipid has advantages that the reagents are added all at once and the colored substance is stable for a long time, the sensitivity is higher than in other lipid determination methods, and the operation is very simple.

In the above two methods of lipid determination of the present invention, the lipid is treated with a surfactant in an aqueous medium. However, the lipid to be determined is not required to be originally in a state of suspension in an aqueous medium. For example, if the sample is solid, the determination is made feasible by treating the solid sample with a prescribed volume of an aqueous surfactant solution.

The composition of the aqueous medium for constituting the reaction system is not particularly limited, if the ionic strength and the pH are within the ranges in which the solubilizing ability of the surfactant is maintained. The unknown sample and the standard sample should be treated at the same pH and the same ionic strength or salt concentration. In the second method of determination of the present invention, the optimum pH value for color reaction is 11.25. Therefore, it is undesirable to use a strongly acidic solution which will shift greatly the pH of the medium to an acidic side.

The procedure of determination of two coexisting components is described below.

The combination of the compound A and the compound B as the two components in the present invention is such that the result of the determination of one component influences the result of the determination of the other component. The two components are selected, in addition to the combination of lipid and protein, from lipids, sugars, nucleic acids, coloring matters, and other various medicines. In the method of the present invention, the sampling amount of an unknown sample can be minimized by introduction of a determination method which does not destroy the sample by reaction, such as absorption measurement, as at least one of the determination methods a and b.

The method of the present invention is described in detail by reference to specific examples where the compound A is a lipid and the compound B is a protein.

Firstly, by the determination method a selected for lipid determination, a calibration curve (a linear function) is prepared for singly existing lipid, and a gradient of the curve (a concentration constant $a_1$) is derived. Then the following equation holds:

$$VLa = La \cdot a_1 \qquad \text{(III)}$$

where La is concentration of the lipid, and VLa is a measured value according to the determination method a.

Secondly, for singly existing protein, a calibration curve (a linear function) is prepared with the determination method a, and a gradient of the curve (a concentration constant $a_2$) is derived. Then the following equation holds:

$$VPa = Pa \cdot a_2 \qquad \text{(IV)}$$

where Pa is concentration of the protein, and VPa is a measured value according to the determination method a.

An unknown sample containing both lipid and protein are analyzed by the determination method a under the same conditions as in preparation of the calibration curves to obtain a measured value Va. Since the unknown sample contains both lipid and protein, the value Va corresponds to an apparent lipid concentration affected by the presence of the protein. Therefore, if the actual lipid concentration is x and the actual protein concentration is y, the following equation is valid from the above equations (III) and (IV):

$$Va = x \cdot a_1 + y \cdot a_2 \qquad \text{(V)}$$

On the other hand, by the determination method b selected for protein determination, a calibration curve (a linear function) is prepared for singly existing lipid, and the gradient of the curve (a concentration constant $b_1$) is derived. Then the following equation holds:

$$VLb = Lb \cdot b_1 \qquad \text{(VI)}$$

where Lb is concentration of the lipid, and VLb is a measured value according to the determination method b.

Further, for singly existing protein, a calibration curve (a linear function) is prepared with the determination method b, and a gradient of the curve (a concentration constant $a_2$) is derived. Then the following equation holds:

$$VPb = Pb \cdot b_2 \qquad \text{(VII)}$$

where Pb is concentration of the protein, and VPb is a measured value according to the determination method b.

An unknown sample containing both lipid and protein are analyzed by the determination method b under the same conditions as in preparation of the calibration curves to obtain a measured value Vb. Since the unknown sample contains both lipid and protein, the value Vb corresponds to an apparent protein concentration affected by the presence of the lipid. Therefore, assuming the actual lipid concentration as x and the actual protein concentration as y, the following equations are valid from the above equations (VI) and (VII):

$$Vb = x \cdot b_1 + y \cdot b_2 \qquad \text{(VIII)}$$

In the above equations (V) and (VIII), the concentration constants have already been determined. Therefore, the actual concentrations of the lipid and the protein can be obtained by applying the measured values to the equations and solving the simultaneous linear equations.

If one of the lipid and the protein is in an extremely smaller amount and is practically negligible according to the applied determination method, the apparent concentration of the other may be regarded as the actual concentration.

Any method of analysis of two-component system of lipid and protein may be employed provided that the above calculation can be applied. For example, for determination of lipid, the first method and the second method above of the present invention are mentioned.

In preparation of the calibration curve in the first method of determination of lipid, ideally, the lipid containing no protein and being in the same form as that in the unknown sample is used as the standard lipid, and a series of solutions of known lipid concentrations are prepared. For example, when the object to be determined is proteoliposome, it is preferred to prepare liposome and provide a known concentration series of the liposome. Practically, however, a simple emulsion of lipid and a surfactant may be used for the calibration instead. When the object to be determined is proteoliposome, a surfactant such as octylglucoside is added to lipid for proteoliposome at a final concentration of 1%; the mixture is subjected to supersonic treatment; and the absorbance is measured at an optical path length of 1 cm at a wavelength of 240 nm. The measured value corresponds to the sum of the absorption caused by the lipid and the octylglucoside. Accordingly, a solution not containing the lipid is treated in the same manner, and contribution of the octylglucoside is calculated to obtain a blank value.

On the other hand, the method for determining protein includes a BCA method, a Lowry method, and the like as mentioned above. In the Lowry method, the calibration curve is prepared by adding an alkaline copper solution respectively to a known amount of lipid or a known amount of protein, leaving the mixture standing for 10 minutes; then mixing a Folin solution thereto; and, after 30 minutes or longer therefrom, measuring the absorbance at 750 nm to prepare the calibration curve. Separately a control solution which contains neither lipid nor protein is prepared, and the absorbance of this solution is subtracted from the absorbance at each concentration of lipid or protein to obtain true calibration curves (linear functions) for the lipid and the protein.

The combination of the method of determination of lipid and the BCA method or the Lowry method advantageously enables quantitative analysis of a sample in which lipid is in a complex structure such as a membrane structure. Further the combination of these determination methods enables, in a simple manner, determination of lipid and protein even in a complicated two-component system such as protein incorporated in a liposome membrane or a vesicle; glass beads or fine polymer particles having lipid and protein adsorbed on the exterior surface thereof; black membranes containing protein; planar bimolecular films containing protein reconstructed by a sticking method or a patch-pipet method, and LB films formed from protein and lipid mixedly.

Incidentally, the first method of determination of lipid does not destroy the sample by reaction with a reagent or other causes. Therefore, the sample subjected to this method of determination can be further subjected to another determination, thereby minimizing the amount of sampling of unknown samples. Further, the combination of the above three methods of determination involves relatively few steps as a whole, and is preferred in view of minimizing the loss of the sample.

The present invention is described in more detail by reference to Examples.

EXAMPLE 1

In an eggplant-shape flask, 0.5 ml of a solution of 30 mg/ml of asolectin (soybean phosphatidylcholine, type IV-S; made by Sigma Co.) in chloroform was placed. The solvent was evaporated off by use of a rotary evaporator, and then completely removed completely in a desiccator in vacuum to form a thin film of lipid. Thereto, 1.0 ml of aqueous 10 mM potassium chloride solution was added and treated with a vortex mixer for 5 minutes to disperse the thin lipid film. Then it was treated with a water-bath type ultrasonic oscillator (Sonifier Type B-15, using cup horn, made by Branson Co.) for 30 minutes to obtain a liposome dispersion (15 mg/ml).

The liquid liposome dispersion thus prepared was found to have a particle size distribution in the range of from 30 to 260 nm (average particle diameter of 190 nm) by use of a dynamic light-scattering particle size analyzer.(DLS-700, Otsuka electronics Co. LTD.)

This liposome dispersion was diluted with aqueous 10 mM potassium chloride solution containing 1% by weight of octylglucoside (n-octyl-$\beta$-D-glucoside; made by Wako Pure Chemical Industries, Ltd.) to various concentrations and the diluted dispersion was treated with the water-bath type supersonic oscillator for one minute to obtain phospholipid standards in a concentration range of from 0 to 1.5 mg/ml.

The standard phospholipid liquid was put into a quartz cell having an optical path of 1 cm, and the absorbance was measured at 240 nm by means of a spectrophotometer (UV-VIS-NIR Recording Spectrophotometer UV 3100S, Shimadzu Corporation). The absorbance values were plotted as a function of the phospholipid concentration by use, as the reference, of the absorbance of aqueous 10 mM potassium chloride solution containing 1% octylglucoside. Thus a straight line passing the origin was obtained. From the gradient of the line, the following relation was valid between the phopholipid concentration and the absorbance:

(Absorbance)=0.400×(phospholipid concentration, mg/ml)

Accordingly, the quantity of phospholipid in an unknown sample can be determined by treating the unknown sample in the same manner as above, measuring the absorbance, and calculating with the above equation.

EXAMPLE 2

A liquid liposome dispersion was prepared in the same manner as in Example 1. The dispersion was frozen by immersion in liquid nitrogen, was thawed by leaving standing at room temperature, then was subjected to supersonic treatment for one minute. This freezing and thawing operation was conducted six times, whereby a liposome liquid dispersion having relatively large particle diameter could be prepared. The particle diameter distribution was found to be in the range of from 130 to 520 nm (average particle diameter: 280 nm) by measurement in the same manner as in Example 1 by means of a dynamic light-scattering particle size analyzer.

The liposome dispersion thus prepared was diluted with an aqueous 10 mM potassium chloride solution containing 1% by weight of octylglucoside in the same manner as in Example 1, the diluted dispersion was treated with the water-bath type supersonic oscillator for one minute in the same manner as in Example 1 to obtain phospholipid standards in a concentration range of from 0 to 1.5 mg/ml.

The absorbance of the standard phospholipid was measured at 240 nm. The absorbance values were plotted as a function of the phospholipid concentration by use, as the reference, of the absorbance of aqueous 10 mM potassium chloride solution containing 1% octylglucoside. Thus a straight line passing the origin was obtained. From the gradient of the line, the following relation was valid between the phopholipid concentration and the absorbance:

(Absorbance)=0.400×(phospholipid concentration, mg/ml)

Accordingly, the quantity of phospholipid in an unknown sample can be determined by treating the unknown sample in the same manner as above, measuring the absorbance, and calculating with the above equation.

EXAMPLE 3

Phospholipid standard liquid was prepared in the concentration range of from 0 to 50 $\mu$g/ml in the same manner as in Example 1.

To each 0.5 ml of the phospholipid standard solutions, an equal amount of a BCA color developing solution (Micro BCA Protein Assay Reagent Kit purchased from Pierce) was added and mixed, and the heated at 60° C. for one hour. The mixture was cooled to room temperature. Absorbance was measured at 562 nm with a cell having optical path of 1 cm. From the measured absorbance, the absorbance of the control containing no liposome was subtracted. The resulting absorbance was plotted taking the absorbance on the ordinate and the liposome concentration on the abscissa. The plots are on a line passing the origin, the gradient of the line being $3.89 \times 10^{-2}$.

Accordingly, the quantity of lipid (X $\mu$g/ml) in an unknown sample can be determined by treating the unknown sample in the same manner as above, measuring the absorbance (Y), and calculating with the relation: $Y=3.89 \times 10^{-2} X$.

EXAMPLE 4

Firstly, samples for preparation of the calibration curves were prepared for respective measurements. Soybean phospholipid (asolectin) corresponding to 15 mg of lipid was put into a test tube of about 130 mm in length and 10 mm in diameter, and 1 ml of aqueous 10 mM potassium chloride solution and 50 $\mu$l of aqueous 20% octylglucoside solution were added thereto. The mixture is treated by means of a water-bath type supersonic oscillator for one minute to disperse the lipid. This suspension of lipid micelles was dispensed to test tubes to provide 10 levels of volume of the suspension varying by 10 $\mu$l serially from 100 $\mu$l to 10 $\mu$l. Separately the control containing no lipid was prepared.

Then to the respective test tubes, 10 mM potassium chloride solution containing 1% octylglucoside was added to make the final volume of each sample to be 1 ml, and each of the diluted sample was treated with a water-bath type supersonic oscillator for one minute. Then the absorbance of the treated sample was measured with a cell of 1 cm at wavelength of 240 nm. An absorbance of 0.0489, which was the absorbance of the control containing no lipid, was subtracted from each of the above measured absorbance values. The resulting absorbance values were plotted on an coordinate taking the absorbance as the ordinate and the lipid concentration as the abscissa. The plots were on a line passing the origin, the gradient $a_1$ of the line being $0.400 \times 10^{-3}$. Accordingly, $$A^L = 0.400 \times 10^{-3} x.$$

where x ($\mu$g/ml) is the final concentration of the lipid in the unknown sample.

The protein used for calibration was the same as the one incorporated in the unknown sample. In this Example, bacteriorhodopsin was used which is a membrane protein. This protein was derived by extracting a purple membrane from a hyperhalophilic bacteria, Halobacterium halobium [Method. enzymol., 31, p667–78 (1974)], and removing lipid from the purple membrane according to the method of K. S. Huang [Proc. Natl., Acad. Sci., USA, 77, p323 (1980)]. An aqueous 10 mM potassium chloride solution containing this bacteriorhodopsin at a concentration of 500 μg/ml was dispensed into 8 test tubes in amounts varying by 2.5 μl from 20 μl to 2.5 μl.

To each of the test tubes, was added 50 μl of aqueous 10 mM potassium chloride solution containing octylglucoside at a concentration of 20%. Further, 10 mM potassium chloride solution was added to each sample to the total volume of 1 ml. The respective mixtures were treated with a water-bath type supersonic oscillator for one minute. The light absorbance thereof was measured at 240 nm with a 1 cm cell. An absorbance of 0.0489, which was the absorbance of the control containing no protein, was subtracted from each of the above measured absorbance values. The resulting absorbance values were plotted on an coordinate taking the absorbance as the ordinate and the protein concentration as the abscissa. The plots were on a line passing the origin, the gradient b1 of the line being $2.7\times10^{-3}$. Accordingly, $$A^P = 2.7 \times 10^{-3} y.$$

where y (μg/ml) is the final concentration of the protein in the unknown sample.

Subsequently, calibration curves for lipid and protein for the Lowry method were prepared. Ten volumes varying by 10 μg from 100 μl to 10 μl of lipid suspension liquid were put into 10 test tubes respectively. To each of them, an aqueous 10 mM potassium chloride solution containing 1% octylglucoside to a final volume of 250 μl. Thereto, was added 500 μl of alkaline copper solution (composed of: 0.2N NaOH containing 4% $Na_2CO_3$ and 2% sodium dodecylsulfate, 2% $CuSO_4 \cdot 5H_2O$, and 4% sodium citrate in the ratio of 100:1:1). The mixture was left standing at room temperature for 15 minutes. Further thereto, 100 μl of the phenol reagent was added, and the mixture was left standing at room temperature for 30 minutes. Then the absorbance was measured at 750 nm. The absorbance was measured with the control solution which contained neither-lipid nor protein. An absorbance of 0.058, which was the absorbance of the control containing no lipid, was subtracted from each of the above measured absorbance values. The resulting absorbance values were plotted on an coordinate taking the absorbance as the ordinate and the lipid concentration as the abscissa. The plots were on a line passing the origin, the gradient $a_2$ of the line being $3.03\times10^{-4}$. Accordingly, $$B^L = 3.03 \times 10^{-4} x$$

where x (μg/ml) is the final concentration of the lipid in the unknown sample.

In the same manner as in the aforementioned protein determination by absorbance, 8 samples were prepared of bacteriorhodopsin. An aqueous 10 mM potassium chloride containing 1% octylglucoside was added to each of the samples to the final volume of 250 μl. Thereto, 500 μl of an alkaline copper solution was added, and the mixture was left standing at room temperature for 15 minutes. Further thereto, 100 μl of the phenol reagent was added, and the mixture was left standing at room temperature for 30 minutes. The absorbance was measured at 750 nm for each of the samples. An absorbance of 0.058, which was the absorbance of the control containing no protein, was subtracted from each of the above measured absorbance values. The resulting absorbance values were plotted on an coordinate taking the absorbance as the ordinate and the protein concentration as the abscissa. The plots were on a line passing the origin, the gradient $b_2$ of the line being $2.99\times10^{-2}$. Accordingly, $$B^P = 2.99 \times 10^{-2} y.$$

where y (μg/ml) is the final concentration of the protein in the unknown sample.

An unknown sample to be subjected to the determination was prepared by coating glass beads with a flat membrane. In this Example, the flat membrane was prepared according the method described in Japanese Patent Application Laid-Open No. 2-59075. Firstly, 0.5 g of porous glass beads (made by Asahi Glass Co., Ltd.; particle diameter: 5 μm, specific surface area: 200 $m^2/g$) were washed with a heated 5% solution of Extran (made by Merck Co.), treated by use of a water-bath type supersonic washer for 30 minutes, washed with flowing water for 30 minutes, and dried in an oven at a temperature of from 110° to 150° C. The dried glass beads were put into a solution composed of 2 ml of octadecyltrichlorosilane, 140 ml of n-hexadecane, 30 ml of carbon tetrachloride, and 20 ml of chloroform, and were stirred therein at room temperature for 2 hours. Then the glass beads were taken out, washed three times with chloroform, and once with ethanol, and dried in an oven at 110° C. As the result, alkyl groups were introduced onto the surface of the glass beads.

Subsequently, proteoliposome was prepared as below. A solution of soybean phospholipid (azolectin) corresponding to 150 mg of lipid in chloroform was placed in a 30-ml eggplant-shape flask. The solvent was evaporated by means of a rotary evaporator, and further completely removed off in a desiccator by vacuum. Thereto, 10 ml of aqueous 100 mM potassium chloride solution was added, and the mixture was treated by use of a vortex mixer for 5 minutes in order to disperse the lipid thin film. The dispersion was further treated by means of a probe-type supersonic oscillator for 30 minutes to prepare a suspension of unilamellar liposome having a mean diameter of 100 nm. 1 mg of bacteriorhodopsin, which is membrane protein, was added to this liposome suspension. This liquid was frozen by liquid nitrogen or dry ice-acetone, thawed at room temperature, and treated by means of a vortex mixer for 30 seconds. This freezing and thawing procedure was repeated six times. Consequently, unilamellar proteoliposome was formed which has an average particle diameter of about 300 nm.

This proteoliposome solution was placed in a development vessel, and the above-prepared alkylated glass beads were immersed therein. In about 30 minutes, the proteoliposome was completely cleaved, and a lipid bilayer flat membrane composed of bacteriorhodopsin-phospholipid was formed on the surface of the glass beads. According to this procedure, the proteoliposome is considered not to penetrate into the pore of the porous glass since the proteoliposome has a particle diameter much larger than the average pore size of the porous glass.

The glass beads coated with bilayer planar membrane containing bacteriorhodopsins were immersed in 1 ml of an aqueous 10 mM potassium chloride solution containing 1% octylglucoside, and were treated by means of a water-bath type supersonic oscillator for 10 minutes. By this treatment, the flat membrane on the surface of the glass beads was eluted from glass beads and the bilayer lipid membrane structure was destroyed into a monomer state. 100 μl of the monomer solution was taken out and was subjected to measurement of absorbance at 240 nm. The absorbance, after subtracting the absorbance 0.048 of the control containing no liposome, was 0.250. In this case, the amount of the protein is much less than the amount of lipid. Therefore, by neglecting the second term in the equation (V):

$$0.250 = 0.400 \times 10^{-3} x$$

$$x = 625$$

Thus the lipid was found to be 625 μg/ml.

Subsequently, determination by the Lowry method was practiced. 100 μl of the above monomer solution, which was derived from the glass beads coated with bimolecular planar membrane, as the unknown sample was diluted withn aqueous 10 mM potassium chloride solution containing 1% octylglucoside to a final volume of 250 μl. Thereto, 500 μl of an alkaline copper solution was added, and the mixture was left standing at room temperature for 15 minutes. Then 100 μl of a phenol reagent was added, and the mixture was left standing at room temperature for 30 minutes. Then the absorbance thereof was measured at 750 nm. The absorbance, after subtraction of the absorbance 0.058 of the control sample and in consideration of dilution ratio, was 0.310. Therefore, $$0.310 = 3.03 \times 10^{-4} x + 2.99 \times 10^{-2} y$$

By substituting the above-derived value, 625 (μg/ml) for x in this equation, the value of y, namely the amount of the protein, was found to be 4.03 (μg/ml).

These values coincided well with the values derived by extraction of the glass beads with a mixture of an organic solvent and an aqueous solvent.

EXAMPLE 5

Samples for preparation of the calibration curves for the respective measurements were prepared firstly. A solution of soybean phospholipid (asolectin) in chloroform corresponding to 15 mg of lipid was put into a test tube of about 10 mm in diameter and about 130 mm in length. The solvent was evaporated with a rotary evaporator, and removed completely in a desiccator in vacuum to form a thin film of lipid on the inside wall of the test tube. Thereto, 1 ml of aqueous 10 mM potassium chloride solution was added, and the content of the test tube was treated by means of a vortex mixer for 5 minutes to disperse the lipid thin film, and then treated by means of a probe-type supersonic oscillator for 30 minutes to form a liquid suspension of unilamellar liposome of 100 nm in average diameter.

Ten fractions of the liposome liquid suspension varying in volume by 10 μl from 100 μl to 10 μl were taken into 10 test tubes respectively. 50 μl of aqueous 10 mM potassium chloride solution containing 20% octylglucoside was added to each of the test tubes. Separately, a sample containing no liposome was also provided as the control. Further, 10 mM potassium chloride solution was added to each sample to the total volume of 1 ml. The respective mixtures were treated with a water-bath type supersonic oscillator for one minute. The light absorbance thereof was measured at 240 nm with a quartz cell having an optical path of 1 cm cell. An absorbance of 0.0489, which was the absorbance of the control containing no liposome, was subtracted from each of the above measured absorbance values. The resulting absorbance values were plotted on an coordinate taking the liposome concentration as the abscissa and the absorbance as the ordinate. The plots were on a line passing the origin, the gradient $a_1$ of the line being $0.400 \times 10^{-3}$. Accordingly, $$A^L = 0.400 \times 10^{-3} x.$$

where x (μg/ml) is the final concentrations of the lipid in the unknown sample.

The protein used for calibration was the same as the one incorporated in an unknown sample. In this Example, bacteriorhodopsin described in Example 4 was used.

The bacteriorhodopsin was suspended in aqueous 10 mM potassium chloride solution at a concentration of 1 mg/ml. The suspension was dispensed into 8 test tubes in amounts varying by 2.5 μl serially from 20 μl 2.5 μl. To each of the test tubes, was added 50 μl of aqueous 10 mM potassium chloride solution containing octylglucoside at a concentration of 20%. Further, 10 mM potassium chloride solution was added to each sample to the total volume of 1 ml and mixed enough. The respective mixtures were treated with a water-bath type supersonic oscillator for one minute. The light absorbance thereof was measured at 240 nm with a quartz cell having an optical path of 1 cm. An absorbance of 0.0489, which was the absorbance of the control containing no protein, was subtracted from each of the above measured absorbance values. The resulting absorbance values were plotted on a coordinate taking the final protein concentration as the abscissa, and the absorbance as the ordinate. The plots were on a line passing the origin, the gradient $b_1$ of the line being $2.70 \times 10^{-3}$. Accordingly, $$A^P = 2.70 \times 10^{-3} y.$$

where y (μg/ml) is the final concentrations of the protein in the unknown sample.

Subsequently, calibration curves for liposome and protein for the BCA method were prepared. The liposome liquid suspension prepared above was dispensed to 10 test tubes in amounts varying by 5 μl serially from 50 μl to 5 μl. To each of them, was added 50 μl of aqueous 10 mM potassium chloride solution containing 20% octylglucoside. Separately, the control sample was also provided which contained no liposome. Further 10 mM potassium chloride solution was added to each sample to the total volume of 1 ml. To each of the test tubes, the BCA color reagent was added in a volume equal to the sample, and the reaction was allowed to proceed at 60° C. for 60 minutes. Then the mixture was cooled to room temperature. The absorbance was measured at room temperature at 562 nm. The absorbance values, after substraction of the absorbance 0.533 of the control containing no liposome, were plotted on an coordinate taking the lipid concentration as the abscissa and the absorbance as the ordinate. The plots were on a line passing the origin, the gradient $a_2$ of the line being $3.89 \times 10^{-2}$. Accordingly, $$B^L = 3.89 \times 10^{-2} x$$

where x (μg/ml) is the final concentrations of the protein in the unknown sample.

In the same manner as in the forementioned protein determination by absorbance, 8 samples were prepared of bacteriorhodopsin, and the final volume was adjusted to 1 ml. To each of the test tubes, the BCA color reagent was added in a volume equal to the sample, and the reaction was allowed to proceed at 60° C. for 60 minutes. Then the mixture was cooled to room temperature. The absorbance was measured at room temperature at 562 nm. The absorbance values, after substraction of the absorbance 0.533 of the control containing no bacteriorhodopsin, were plotted on an coordinate taking the bacteriorhodopsin concentration as the abscissa and the absorbance as the ordinate. The plots were on a line passing the origin, the gradient $b_2$ of the line being $9.63\times10^{-2}$. Accordingly, $$B^P = 9.63\times10^{-2} Y.$$

where y ($\mu$g/ml) is the final concentration of the protein in the unknown sample.

As an unknown sample, a proteoliposome sample was prepared. A liposome liquid suspension was prepared which contained lipid 15 mg/ml according to the method described above. This liposome liquid suspension was diluted tenfold with aqueous 10 mM potassium chloride solution. 133 $\mu$l of this diluted suspension (equivalent to 200 $\mu$l) was taken out, and thereto 40 $\mu$g of bacteriorhodopsin, which is membrane protein; was added. The mixture was treated by means of a water-bath type supersonic oscillator for 30 seconds. The proteoliposome prepared in such a manner was diluted to a final volume of 200 $\mu$l with aqueous 10 mM potassium chloride solution containing 1% octylglucoside, and treated by a water-bath type supersonic oscillator for one minute. Then the absorbance was measured at 240 nm. The absorbance, after subtraction of the absorbance of 0.0489 of the control containing no proteoliposome, was 0.94. Therefore the equation below was valid in consideration of the dilution ratio:

$$0.94\times10 = 0.400\times10^{-3}x + 2.70\times10^{-3}y$$

Then determination was conducted according to the BCA method. The unknown sample which had been used in the above absorbance measurement was further diluted to final volume of 500 $\mu$l with aqueous 10 mM potassium chloride solution containing 1% octylglucoside. Thereto the BCA color reagent was added in a volume equal to the sample solution. The reaction was allowed to proceed at 60° C. for 60 minutes. The mixture was cooled to room temperature. The absorbance was measured at room temperature at 562 nm. The absorbance, after subtraction of the absorbance of 0.533 of the control containing no proteoliposome, was 1.16. Therefore the equation below was valid in consideration of the dilution ratio:

$$1.16\times50 = 3.89\times10^{-2}x + 9.63\times10^{-2}y$$

The values of x and y were obtained from the above equations in consideration of dilution ratio. The value of x, namely the amount of the lipid, was found to be 1000 ($\mu$g/ml), and the value of y, namely the amount of the protein, was found to be 200 ($\mu$g/ml). These values coincide with the amount of 200 $\mu$g of lipid and 40 $\mu$g of protein (both in 200 $\mu$l) at the preparation of proteoliposome.

EXAMPLE 6

Samples for preparation of the calibration curves for the respective measurements were firstly prepared. A solution of soybean phospholipid (asolectin) in chloroform corresponding to 15 mg of lipid was put into a test tube of about 10 mm in diameter and about 130 mm in length. The solvent was evaporated with a rotary evaporator, and removed completely in a desiccator in vacuum. Thereto, 1 ml of aqueous 10 mM potassium chloride solution was added, and the content of the test tube was treated by means of a vortex mixer for 5 minutes to disperse the lipid thin film formed therein, and then treated by means of a probe-type supersonic oscillator for 30 minutes to form a liquid suspension of unilamellar liposome of 100 nm in average diameter.

Ten fractions of the liposome liquid suspension varying in volume by 10 $\mu$l serially from 100 $\mu$l to 10 $\mu$l were taken into 10 test tubes respectively. 50 $\mu$l of aqueous 10 mM potassium chloride solution containing 20% octylglucoside was added to each of the test tubes. Separately, a sample containing no liposome was also provided as the control. Further aqueous 10 mM potassium chloride solution was added to each sample to the total volume of 1 ml. The respective mixtures were treated with a water-bath type supersonic oscillator for one minute. The light absorbance thereof was measured at 240 nm with a quartz cell having an optical path of 1 cm. An absorbance of 0.0489, which was the absorbance of the control containing no liposome, was subtracted from each of the above measured absorbance values. The resulting absorbance values were plotted on an coordinate taking the liposome concentration as the abscissa and the absorbance as the ordinate. The plots were on a line passing the origin, the gradient $a_1$ of the line being $0.400\times10^{-3}$. Accordingly, $$A^L = 0.400\times10^{-3}x.$$

where x ($\mu$g/ml) is the final concentrations of the lipid in the unknown sample.

The protein used for calibration was the same as the one incorporated in an unknown sample. In this Example, bacteriorhodopsin described in Example 4 was used.

The bacteriorhodopsin was suspended in aqueous 10 mM potassium chloride solution at a concentration of 100 mg/ml. The suspension was dispensed into 8 test tubes in amounts varying by 2.5 $\mu$l serially from 20 $\mu$l to 2.5 $\mu$l. To each of the test tubes, was added 50 $\mu$l of aqueous 10 mM potassium chloride solution containing 20% octylglucoside. Further, 10 mM potassium chloride solution was added to each sample to the total volume of 1 ml. The respective mixtures were treated with a water-bath type supersonic oscillator for one minute. The absorbance thereof was measured at 240 nm with a quartz cell having an optical path of 1 cm. An absorbance of 0.0489, which was the absorbance of the control containing no protein, was subtracted from each of the above measured absorbance values. The resulting absorbance values were plotted on an coordinate taking the protein concentration as the abscissa, and the absorbance as the ordinate. The plots were on a line passing the origin, the gradient $b_1$ of the line being $2.70\times10^{-3}$. Accordingly, $$A^P = 2.70\times10^{-3}y.$$

where y ($\mu$g/ml) is the final concentrations of the protein in the unknown sample.

Subsequently, calibration curves for liposome and protein for the Lowry method were prepared. Ten volumes varying by 10 $\mu$l serially from 100 $\mu$l to 10 $\mu$l of lipid suspension liquid were put into 10 test tubes respectively. To each of them, aqueous 10 mM potassium chloride solution containing 1% octylglucoside was added to a final volume of 250 $\mu$l. Thereto, was added 500 $\mu$l of alkaline copper solution (composed of 0.2N NaOH containing 4% $Na_2CO_3$ and 2% sodium dodecylsulfate, 2% $CuSO_4.5H_2O$, and 4% sodium citrate in the ratio of 100:1:1). The mixture was left standing at room temperature for 15 minutes. Further thereto, 100 $\mu$l of the phenol reagent was added, and the mixture was left standing at room temperature for 30 minutes. Then the absorbance was measured at 750 nm. The absorbance was measured also with the control solution which contained neither lipid nor protein. An absorbance 0.058, which was the absorbance of the control containing no lipid, was subtracted from each of the above measured absorbance values. The resulting absorbance values were plotted on an coordinate taking the absorbance as the ordinate and the lipid concentration as the abscissa. The plots were on a line passing the origin, the gradient $a_2$ of the line being $3.03 \times 10^{-4}$. Accordingly, $$B^L = 3.03 \times 10^{-4} x$$

where x (μg/ml) is the final concentration of the lipid in the unknown sample.

In the same manner as in the aforementioned protein determination by absorbance, 8 samples were prepared of bacteriorhodopsin. An aqueous 10 mM potassium chloride containing 1% octylglucoside was added to each of the samples to the final volume of 250 μl. Thereto, 500 μl of an alkaline copper solution was added, and the mixture was left standing at room temperature for 15 minutes. Further thereto, 100 μl of the phenol reagent was added, and the mixture was left standing at room temperature for 30 minutes. Then the absorbance was measured at 750 nm of each of the samples. The absorbance 0.058, which was the absorbance of the control containing no protein, was subtracted from each of the above measured absorbance values. The resulting absorbance values were plotted on a coordinate taking the absorbance as the ordinate and the protein concentration as the abscissa. The plots were on a line passing the origin, the gradient $b_2$ of the line being $2.99 \times 10^{-2}$. Accordingly, $$B^P = 2.99 \times 10^{-2} y.$$

where y (μg/ml) is the final concentration of the protein in the unknown sample.

As an unknown sample, a proteoliposome sample was prepared. A solution of soybean phospholipid (asolectin) in chloroform corresponding to 360 μg of lipid was put into a test tube of about 10 mm in diameter and about 130 mm in length. The solvent was evaporated with a rotary evaporator, and removed completely in a desiccator in vacuum. Thereto, 1 ml of aqueous 10 mM potassium chloride solution was added, and the content of the test tube was treated by means of a vortex mixer for 5 minutes to disperse the lipid thin film formed therein, and then treated by means of a probe-type supersonic oscillator for 30 minutes to form a liquid suspension of unilamellar liposome of 100 nm in average diameter.

To this liposome suspension, was added 10 μg of bactriothodpsin which is a membrane protein. This liquid was frozen in liquid nitrogen or dry ice-acetone, thawed at room temperature, and treated by means of a vortex mixer for 30 seconds. This procedure was repeated six times. Consequently, proteoliposome was formed which has an average particle diameter of about 300 nm.

To 100 μl of this proteoliposome solution, 5 μl of an aqueous 10 mM potassium chloride solution containing 20% octylglucoside was added, and the mixture was treated by means of a water-bath type supersonic oscillator for one minutes. Then the absorbance was measured at 240 nm. The absorbance, after subtraction of the absorbance 0.0489 of the control sample containing no liposome in consideration of the dilution ratio, was 0.160. Therefore, $$0.160 = 0.400 \times 10^{-3} x + 2.70 \times 10^{-3} y$$

Subsequently, determination by the Lowry method was practiced. The proteoliposome solution (105 μl), which had been used for determination of lipid, as the unknown sample was diluted with aqueous 10 mM potassium chloride solution containing 1% octylglucoside to a total volume of 250 μl. Thereto, 500 μl of alkaline copper solution was added, and the mixture was left standing at room temperature for 15 minutes. 100 μl of a phenol reagent was added thereto, and the mixture was left standing at room temperature for 30 minutes. Then the absorbance thereof was measured at 750 nm. The absorbance, after subtraction of the absorbance 0.058 of the control sample and in consideration of dilution ratio, was 0.358. Therefore, $$0.358 = 3.03 \times 10^{-4} x + 2.99 \times 10^{-2} y$$

The values of x and y were obtained from the above equations. The value of x, namely the amount of the lipid, was found to be 342 (μg/ml), and the value of y, namely the amount of the protein, was found to be 8.50 (μg/ml). These values coincide roughly to 360 μg of the lipid and 10 μg of the protein added at the preparation of the sample.

EXAMPLE 7

Four calibration curves for standard solution containing lipid or protein were obtained by two methods of determination in the same manner as in Example 6.

As an unknown sample, a proteoliposome sample was prepared. A solution of soybean phospholipid (asolectin) in chloroform corresponding to 600 μg of lipid was put into a test tube of about 10 mm in diameter and about 130 mm in length. The solvent was evaporated with a rotary evaporator, and removed completely in a desiccator in vacuum. Thereto, 1 ml of aqueous 10 mM potassium chloride solution was added, and the content of the test tube was treated by means of a vortex mixer for 5 minutes to disperse the lipid thin film formed therein, and then treated by means of a probe-type supersonic oscillator for 30 minutes to form a liquid suspension of unilamellar liposome of 100 nm in average diameter.

To this liposome suspension, was added 5 μg of bactriothodpsin which is a membrane protein. This liquid was frozen in liquid nitrogen or in dry ice-acetone, thawed at room temperature, and treated by means of a vortex mixer for 30 seconds. This freeze and thaw procedure was repeated six times. Consequently, proteoliposome was formed which has an average particle diameter of about 300 nm.

To 100 μl of this proteoliposome solution, 5 μl of aqueous 10 mM potassium chloride solution containing 20% octylglucoside was added, and the mixture was treated by means of a water-bath type supersonic oscillator for one minutes. Then the absorbance was measured at 240 nm. The absorbance, after subtraction of the absorbance 0.0489 of the control sample containing no proteoliposome, was 0.25. In this system, the ratio of the lipid to the protein was 120:1, therefore the amount of the protein was considered to be negligible in comparison with the amount of the lipid. Accordingly, $$0.25 = 0.400 \times 10^{-3} x$$

$$x = 625 \text{ (μg/ml)}$$

Subsequently, determination by the Lowry method was practiced. 100 μl of the proteoliposome solution, which was used for determination of lipid, as the unknown sample was diluted with aqueous 10 mM potassium chloride solution containing 1% octylglucoside to a total volume of 250 μl. Thereto, 500 μl of an alkaline copper solution was added, and the mixture was left standing at room temperature for 15 minutes. 100 μl of a phenol reagent was added thereto, and the mixture was left standing at room temperature for 30 minutes. Then the absorbance thereof was measured at 750 nm. The absorbance, after subtraction of the absorbance 0.058 of the control sample and in consideration of dilution ratio, was 0.335. Therefore, $$0.335=3.03\times10^{-4}x+2.99\times10^{-2}y$$

The values of y, namely the amount of the protein, was found to be 4.90 (μg/ml) by substituting 625 μg/ml for x in the above equation. The values of x and y coincide roughly to 600 μg of the lipid and 5 μg of the protein added at the preparation of the sample.

EXAMPLE 8

The calibration curves were obtained by 240 nm-absorbance method and BCA method to measure standard solution independently containing lipid or protein. A liquid suspension of soybean phospholipid (asolectin, 15 mg/ml) was dispensed to 10 test tubes in amounts varying by 10 μl serially from 100 μl to 10 μg. To each of the test tubes, was added 50 μl of aqueous 10 mM potassium chloride solution containing 20% octylglucoside. Separately, a control sample containing no lipid was provided. Then to the respective test tubes, aqueous 10 mM potassium chloride solution was added to make the final volume of each sample came to be 1 ml, and each of the diluted sample was treated with a water-bath type supersonic oscillator for one minute. Then the absorbance of the treated sample was measured with a quartz cell of 1 cm at wavelength of 240 nm. An absorbance of 0.0489, which was the absorbance of the control containing no lipid, was subtracted from each of the above measured absorbance values. The resulting absorbance values were plotted on an coordinate taking the absorbance as the ordinate and the lipid concentration as the abscissa. The plots were on a line passing the origin, the gradient $a_1$ of the line being $0.400\times10^{-3}$. Accordingly, $$A^L=0.400\times10^{-3}x.$$

where x (μg/ml) is the final concentrations of the lipid in the unknown sample.

The protein used for calibration was the same one incorporated in the sample of unknown concentration. In this Example, bacteriorhodopsin was used which is a membrane protein. This protein was derived by extracting a purple membrane from a hyperhalophilic bacteria, Halobacterium halobium [Method. Enzymol., 31, p667–78 (1974)], and removing lipid from the purple membrane according to the method of K. S. Huang [Proc. Natl., Acad. Sci., USA, 77, p323 (1980)].

The bacteriorhodopsin obtained above was suspended in aqueous 10 mM potassium chloride solution at a concentration of 1 mg/ml. This suspension was dispensed into 8 test tubes in amounts varying by 2.5 μl serially from 20 μl to 2.5 μl. To each of the test tubes, was added 50 μl of aqueous 10 mM potassium chloride solution containing 20% octylglucoside. Further, 10 mM potassium chloride solution was added to each sample to the total volume of 1 ml. The respective mixtures were treated with a water-bath type supersonic oscillator for one minute. The light absorbance thereof was measured at 240 nm with a 1 cm quartz cell. An absorbance of 0.0489, which was the absorbance of the control containing no protein, was subtracted from each of the above measured absorbance values. The resulting absorbance values were plotted on a coordinate taking the absorbance as the ordinate and the protein concentration as the abscissa. The plots were on a line passing the origin, the gradient $b_1$ of the line being $2.70\times10^{-3}$. Accordingly, $$A^P=2.70\times10^{-3}y.$$

where y (μg/ml) is the final concentration of the protein in the unknown sample.

Subsequently, calibration curves for lipid and protein for the BCA method were prepared. The lipid liquid suspension prepared above was dispensed to 10 test tubes in amounts varying by 5 μl serially from 50 μl to 5 μl. To each of them, was added 50 μl of aqueous 10 mM potassium chloride solution containing 20% octylglucoside. Then to the respective test tubes, aqueous 10 mM potassium chloride solution was added to make the final volume to be 1 ml. Separately, the control sample was also provided which contained no liposome. To each of the test tubes, the BCA color reagent was added in a volume equal to the sample, and the reaction was allowed to proceed at 60° C. for 60 minutes. Then the mixture was cooled to room temperature. The absorbance was measured at 562 nm. The absorbance values, after substraction of the absorbance 0.533 of the control containing no lipid, were plotted on an coordinate taking the lipid concentration as the abscissa and the absorbance as the ordinate. The plots were on a line passing the origin, the gradient $a_2$ of the line being $3.89\times10^{-2}$. Accordingly, $$B^L=3.89\times10^{-2}x$$

where x (μg/ml) is the final concentrations of the lipid in the unknown sample.

In the same manner as in the forementioned protein determination by absorbance at 240 nm, 8 samples were prepared of bacteriorhodopsin, and the final volume was adjusted to 1 ml. To each of the test tubes, the BCA color reagent was added in a volume equal to the sample, and the reaction was allowed to proceed at 60° C. for 60 minutes. Then the mixture was cooled to room temperature. The absorbance was measured at room temperature at 562 nm. The absorbance values, after substraction of the absorbance 0.533 of the control containing no bacteriorhodopsin, were plotted on an coordinate taking the bacteriorhodopsin concentration as the abscissa and the absorbance as the ordinate. The plots were on a line passing the origin, the gradient $b_2$ of the line being $9.63\times10^{-2}$. Accordingly, $$B^P=9.63\times10^{-2}y$$

where y (μg/ml) is the final concentration of the protein in the unknown sample.

An LB built-up film was prepared as an unknown sample. One milliliter of a solution of soybean phospholipid (asolectin, 15 mg/ml) in chloroform was put in a test tube of 10 mm in diameter and 130 mm in length. The solvent was evaporated by use of a rotary evaporator, and then completely removed in a desiccator in vacuum to form a lipid thin film on the inside wall of the test tube. Thereto, 1 ml of an aqueous 10 mM potassium chloride solution was added, and the content of the test tube was treated by means of a voltex mixer for 5 minutes to disperse the lipid thin film formed therein, and then treated by means of a probe-type supersonic oscillator for 30 minutes to form a liquid suspension of unilamellar liposome of 100 nm in average diameter. 3 mg of bacteriorhodopsin, a membrane protein, was added to the liposome suspension, and the suspension was treated by use of a water-bath type supersonic oscillator for 30 seconds.

100 μl of the proteoliposome suspension was dropped into an LB film-forming trough holding an aqueous 10 mM potassium chloride and 20 mM calcium chloride solution, and the solution was stirred gently for 30 minutes. Thereby the liposome suspension containing the bacteriorhodopsin was cleaved and developed in a monolayer film on the air-liquid interface. The surface pressure of the film was maintained at an appropriate value by limiting the development area of the film not to spread excessively by use of a separator or a float. With this surface pressure maintained, a clean substrate (glass substrate of 45 mm square, having been treated for hydrophilicity with Corning #7059) was immersed and pulled out slowly in a vertical direction. By this procedure, the orientation of the hydrophilic group and the hydrophobic group of the lipid film is reversed at the upward movement and the downward movement of the substrate, thus a "Y type film" is formed in which hydrophobic portions of one layer face to hydrophobic portions of another layer and hydrophilic portions of one layer face to hydrophilic portions of another layer between the layers. Thus, 200 layers of the monolayer film, namely 100 layers of the bilayer film were built up. The same built-up films were prepared on four substrates. The substrates were taken out slowly. Then the four substrates were immersed in 0.2 ml of aqueous 10 mM potassium chloride solution containing 1% octylglucoside. The solution was stirred gently at room temperature for 60 minutes, and subsequently treated by use of a water-bath type supersonic oscillator for one minute. 0.2 ml of the solution was taken out, and the absorbance thereof was measured at 240 nm. The absorbance, after subtraction of the absorbance of 0.0489 of the control containing neither lipid nor protein and in consideration of dilution ratio, was 0.212. Therefore the equation below was valid:

$$0.212=0.400\times10^{-3}x+2.70\times10^{-3}y$$

Then determination was conducted according to the BCA method. The unknown sample which had been used in the above absorbance measurement was further diluted fivefold to give an aqueous 10 mM potassium chloride solution containing 1% octylglucoside. Thereto the BCA color reagent was added in a volume equal to the sample solution. The reaction was allowed to proceed at 60° C. for 60 minutes. The mixture was cooled to room temperature. The absorbance was measured at 562 nm. The absorbance, after subtraction of the absorbance of 0.533 of the control containing no proteoliposome, was 1.31. Therefore the equation below was valid in consideration of the dilution ratio:

$$1.31\times10^{-3}=3.89\times10^{-2}x+9.63\times10^{-2}y$$

The values of x and y were obtained from the above equations. The value of x, namely the amount of the lipid, was found to be 225 ($\mu$g/ml), and the value of y, namely the amount of the protein, was found to be 45 ($\mu$g/ml). These values coincide with the ratio of the lipid to the protein (15 mg:3 mg) used in the preparation of the LB built-up film.

EXAMPLE 9

Lipid and protein were determined of liver cell mitochondria of a guinea pig. At first, the calibration curves had to be obtained with known amounts of lipid and protein. Generally, in the analysis of a natural object, its lipid constituents and the protein constituents are not known. Therefore it is impossible to use the same lipid and protein constituents as those in unknown samples in preparation of the calibration curves. In this Example, therefore, the calibration curves were obtained by use of commercially available lipid and protein. Thereby the amounts of lipid and protein in the mitochondria sample were approximately determined, and the accuracy of the determination was investigated by comparing the obtained values with reported values. Thus, soybean phospholipid (azolectin) and BSA (bovine serum albumin) were used for the calibration of the lipid and the protein.

The calibration curve for lipid was prepared by use of soybean phospholipid. A solution of soybean phospholipid corresponding to 3 mg of lipid in chloroform was put into a test tube. The solvent was evaporated off by use of a rotary evaporator, and then completely removed by vacuum. Thereto, 1 ml of 10 mM potassium chloride solution containing 1% octylglucoside (pH: 5.6) was added and the evaporated residue was dissolved.

For the calibration curve of the BCA method, 0.5 ml of this solution was taken out, and was diluted fifty-fold with aqueous 10 mM potassium chloride solution containing 1% octylglucoside. This diluted solution was further diluted in several steps to prepare samples for the calibration. To each of the diluted sample, an equal amount of the BCA color reagent was added and mixed. The mixture was heated to 60° C. for 60 minutes. After cooling to room temperature, the absorbance of the sample was measured at 562 nm with a cell of optical path of 1 cm. The absorbance values, after subtraction of the absorbance of the control containing no lipid, were plotted on an coordinate taking the lipid concentration as the abscissa and the absorbance as the ordinate. The plots were on a line passing the origin, the gradient $a_1$ being $3.89\times10^{-2}$. Accordingly, $$A^L=3.89\times10^{-2}x$$

where x ($\mu$g/ml) is the concentration of the lipid in the unknown sample.

The remaining 0.5 ml of the solution was used for calibration for the Lowry method. The sample was diluted in several steps to prepare the samples for the calibration. To the sample, an alkaline copper solution was added in a double amount of the sample solution. The mixture was left standing at room temperature for 15 minutes. Thereto, the phenol reagent (commercial reagent diluted twofold with water) was added in an amount of 0.4 volume of the sample solution. The mixture was left standing at room temperature for 30 minutes. The absorbance was measured at 750 nm. The measured absorbance values were plotted in the same manner as in the BCA method. The gradient of the line $a_2$ was $3.03\times10^{-4}$. Therefore, $$B^L=3.03\times10^{-4}x$$

Subsequently, calibration curve of protein was prepared by use of BSA (bovine serum albumin). An aqueous solution of bovine serum albumin was prepared at a concentration of 50 $\mu$g/ml. This solution was diluted in the same manner as in the case of the lipid to give final concentrations of 10 mM potassium chloride and 1% octylglucoside. The colors were developed by the BCA method and the Lowry method, and the absorption was measured in the same manner as of the lipid. The plotting of the measured values gave $b_1$ and $b_2$ respectively of $9.63\times10^{-2}$, and $2.99\times10^{-2}$. Accordingly, $$A^P=9.63\times10^{-2}y$$

$$B^P=2.99\times10^{-2}y$$

where y ($\mu$g/ml) is the protein concentration. Therefore, $A^{L+P}$, and $B^{L+P}$ are shown by following equations:

$$A^{L+P}=3.89\times10^{-2}x+9.63\times10^{-2}y$$

$$B^{L+P}=3.03\times10^{-4}x+2.99\times10^{-2}y$$

The unknown sample of mitochondria was prepared from a liver of a guinea pig. The liver of a guinea pig was taken out so as not to be contaminated by an adjacent tissue insofar as possible. It was washed slightly in in aqueous 250 mM sucrose solution, cut finely by scissors, and treated with a glass homogenizer. Thereto 250 mM of sucrose was added to form as 10% suspension. This suspension was centrifuged at 600×g for 10 minutes, and the supernatant liquid was further centrifuged at 5500×g for 20 minutes to collect the precipitate. The precipitate was again suspended in 250 mM sucrose solution, and centrifuged at 6000×g for 15 minutes. This collected precipitate was once more centrifuged at 6000×g for 15 minutes to obtain a mitochodria fraction. To this precipitated mitochondria, a solution of 10 mM potassium chloride containing 1% octylglcoside was added in an amount of 10 ml per gram of the original liver cells, and stirred well to dissolve the mitochondria. As necessary, the mixture was treated with a water-bath type supersonic oscillator for complete dissolution. This solution was used as the unknown sample.

This sample was diluted 100-fold with an aqueous solution of 10 mM potassium chloride and 1% octylglucoside. 0.5 ml of this sample was subjected to measurement by the BCA method. The absorbance of ($A^{L+P}$), after subtraction of the absorbance 0.533 of the control containing no sample, was 1.23. Accordingly, $$1.23 \times 200 = 3.89 \times 10^{-2} x + 9.63 \times 10^{-2} y$$

where the factor 200 on the left side corresponds to the dilution ratio.

The unknown sample was diluted 30-fold. 0.5 ml of the diluted solution was subjected to measurement by the Lowry method. The absorbance of ($B^{L+P}$), after subtraction of the absorbance 0.058 of the control containing no sample, was 1.20. Accordingly, $$1.20 \times 60 = 3.03 \times 10^{-4} x + 2.99 \times 10^{-2} y$$

The values of x and y were derived by solving the above simultaneous equations.

$$x = 3.71 \times 10^2$$

$$y = 2.40 \times 10^3$$

The ratio of lipid to protein was approximately 1:6.43, which means that one gram of the liver cell contained 24 mg of mitochondria protein. This coincides approximately to the reported values (ratio of entire lipid to protein being 1:6.30, and protein content being 15 to 30 mg per gram of liver cells, in guinea pig liver cells).

EXAMPLE 10

In order to obtain the calibration curves, standard solution of lipid or protein for the respective measurements were prepared firstly. A solution of soybean phospholipid (asolectin) in chloroform corresponding to 15 mg of lipid was put into a test tube of about 10 mm in diameter and about 130 mm in length. The solvent was evaporated with a rotary evaporator, and removed completely by vacuum. Thereto, 1 ml of aqueous 10 mM potassium chloride solution was added, and the content of the test tube was treated by means of a vortex mixer for 5 minutes to disperse the lipid thin film formed therein, and then treated by means of a probe-type supersonic oscillator for 30 minutes to form a liquid suspension of unilamellar liposome of 100 nm in average diameter.

Fractions of the liposome liquid suspension varying serially in volume from 100 $\mu$l to 10 $\mu$l were taken into test tubes respectively. 50 $\mu$l of an aqueous 10 mM potassium chloride solution containing 20% octylglucoside was added to each of the test tubes. Separately, a sample containing no liposome was also provided as the control. Further, 10 mM potassium chloride solution was added to each sample to the total volume of 1 ml. The respective mixtures were treated with a water-bath type supersonic oscillator for one minute.

For the calibration by the BCA method, 0.5 ml each of these samples was taken out, and was diluted 30-fold with aqueous 10 mM potassium chloride solution containing 1% octylglucoside. To 0.5 ml of the diluted sample, an equal amount of the BCA color reagent was added and mixed. The mixture was heated to 60° C. for 60 minutes. After cooling to room temperature, the absorbance of the sample was measured at 562 nm with a cell of optical path of 1 cm. The absorbance values, after subtraction of the absorbance of the control containing no liposome, were plotted on an coordinate taking the lipid concentration as the abscissa and the absorbance as the ordinate. The plots were on a line passing the origin, the gradient $a_1$ being $3.89 \times 10^{-2}$. Accordingly, $$A^L = 3.89 \times 10^{-2} x$$

where x ($\mu$g/ml) is the concentration of the lipid in the unknown sample.

The remaining 0.5 ml of the solution was used for calibration by the Lowry method. To 0.5 ml of the sample, 1.00 ml of the alkaline copper solution was added. The mixture was left standing at room temperature for 15 minutes. Thereto, 0.20 ml of the phenol reagent (commercial reagent diluted two fold) was added. The mixture was left standing at room temperature for 30 minutes. The absorbance was measured at 750 nm. The measured absorbance values were plotted in the same manner as in the BCA method. The gradient of the line $a_2$ was $3.03 \times 10^{-4}$. Therefore, $$B^L = 3.03 \times 10^{-4} x$$

Subsequently, calibration curve of protein was obtained by use of the same protein as in the unknown sample. In this Example, bacteriorhodopsin, a membrane protein in Example 4, was used. This bacteriorhodopsin was dissolved at a concentration of 20 $\mu$g/ml, and was further diluted in several steps to provide samples for calibration. These samples were adjusted as in the case of the lipid to give final concentrations of 10 mM potassium chloride and 1% octylglucoside. The colors were developed by the BCA method and the Lowry method, and the absorption was measured in the same manner as of the lipid. The plotting of the measured values gave $b_1$ and $b_2$ respectively of $9.63 \times 10^{-2}$, and $2.99 \times 10^{-2}$. Accordingly, $$A^P = 9.63 \times 10^{-2} y$$

$$B^P = 2.99 \times 10^{-2} y$$

where y($\mu$g/ml) is the final concentration of the protein in the unknown sample. Therefore, $A^{L+P}$, and $B^{L+P}$, the absorbance of coexisting system are shown by following equations:

$$A^{L+P} = 3.89 \times 10^{-2} x + 9.63 \times 10^{-2} y \qquad (3)$$

$$B^{L+P} = 3.03 \times 10^{-4} x + 2.99 \times 10^{-2} y \qquad (4)$$

As an unknown sample, a proteoliposome sample was prepared. A liposome liquid suspension (lipid content: 15 mg/ml) was prepared according to the method described above. This liposome liquid suspension was diluted tenfold with aqueous 10 mM potassium chloride solution. 300 µl of this diluted suspension (equivalent to 450 µg of lipid) was taken out, and thereto 45 µg of bacteriorhodopsin, was added. The mixture was treated by means of a water-bath type supersonic oscillator for 30 seconds, and stirred gently at room temperature for 2 hours. The proteoliposome prepared in such a manner was diluted to a volume of 1 ml and to give a final concentration of 10 mM potassium chloride and 1% octylglucoside, and treated by a water-bath type supersonic oscillator for one minute.

50 µl of the unknown sample was taken out, diluted with an aqueous solution of 10 mM potassium chloride and 1% octylglucoside, and was subjected to measurement by te BCA method. The absorbance of $A^{L+P}$, after subtraction of the absorbance 0.533 of the control containing no proteoliposome, was 1.09. Accordingly, $$1.09 \times 20 = 3.89 \times 10^{-2}x + 9.63 \times 10^{-2}y \quad (5)$$

where the factor 20 on the left side corresponds to the dilution ratio.

0.5 ml of the remaining unknown sample was subjected to measurement by the Lowry method. The absorbance of $B^{L+P}$, after subtraction of the absorbance 0.058 of the control containing no proteoliposome, was 0.743. Accordingly, $$0.743 \times 2 = 3.03 \times 10^{-4}x + 2.99 \times 10^{-2}y \quad (5)$$

The values of x and y were derived by solving the above simultaneous equations.

$x = 449$ $y = 45$

These values coincide to 450 µg of the lipid and 45 µg of the protein used in the preparation of the proteoliposome.

EXAMPLE 11

Proteoliposome which incorporates bacteriorhodopsin was prepared in the same manner as in Example 6 except that the ratio of the phospholipid to protein was 60. The prepared proteoliposome was fractionated by gel filtration chromatography. Bio Rad A150m (made by Bio Rad Co.) was used as an inert support for gel filtration chromatography. The column had a diameter of 1 cm and a length of 40 cm. The column was preliminarily equilibrated with aqueous 10 mM potassium chloride solution. The amount of the sample put into the column was ca. 600 µl. The flow rate was about 13.3 µl/min. Fractions of 15 drops (about 300 µl) respectively were collected.

50 µl samples from each fractions were taken into Eppendorf tubes respectively. Thereto, 140 µl of 10 mM potassium chloride solution and 10 µl of aqueous 20% octylglucoside solution were added. The mixtures were respectively treated with a water-bath type supersonic oscillator for one minutes. The solubilized samples were subjected to measurement of absorption at 240 nm. The samples after the absorbance measurement were recovered and subjected to the measurement by the Lowry method. The lipid and the protein of each of the fractions was determined by simultaneous equations employing the measured absorbance values, $Abs^{240}$ and $Abs^{Lowry}$. The results of the determination of the fractions are shown in FIG. 1.

COMPARATIVE EXAMPLE 1

The protein in the each fractions obtained in Example 11 was determined by a conventional method in which proteins and lipid are separated before determination.

50 µl samples were taken into Eppendorf tubes respectively. Thereto, 1 ml of methanol was added. The mixture was subjected to vortex treatment, and then centrifuged at 15000 rpm for 20 minutes to recover precipitate. 1 ml of a mixed solvent composed of toluene and diethyl ether (2:1) was added to the precipitate, and the precipitate was dispersed by vortex treatment. The precipitate was recovered by centrifuge again. The recovered precipitate was dissolved in 50 µl of aqueous 1% sodium dodecylsulfate solution, and was subjected to determination of protein according the Lowry method.

Figure 2:
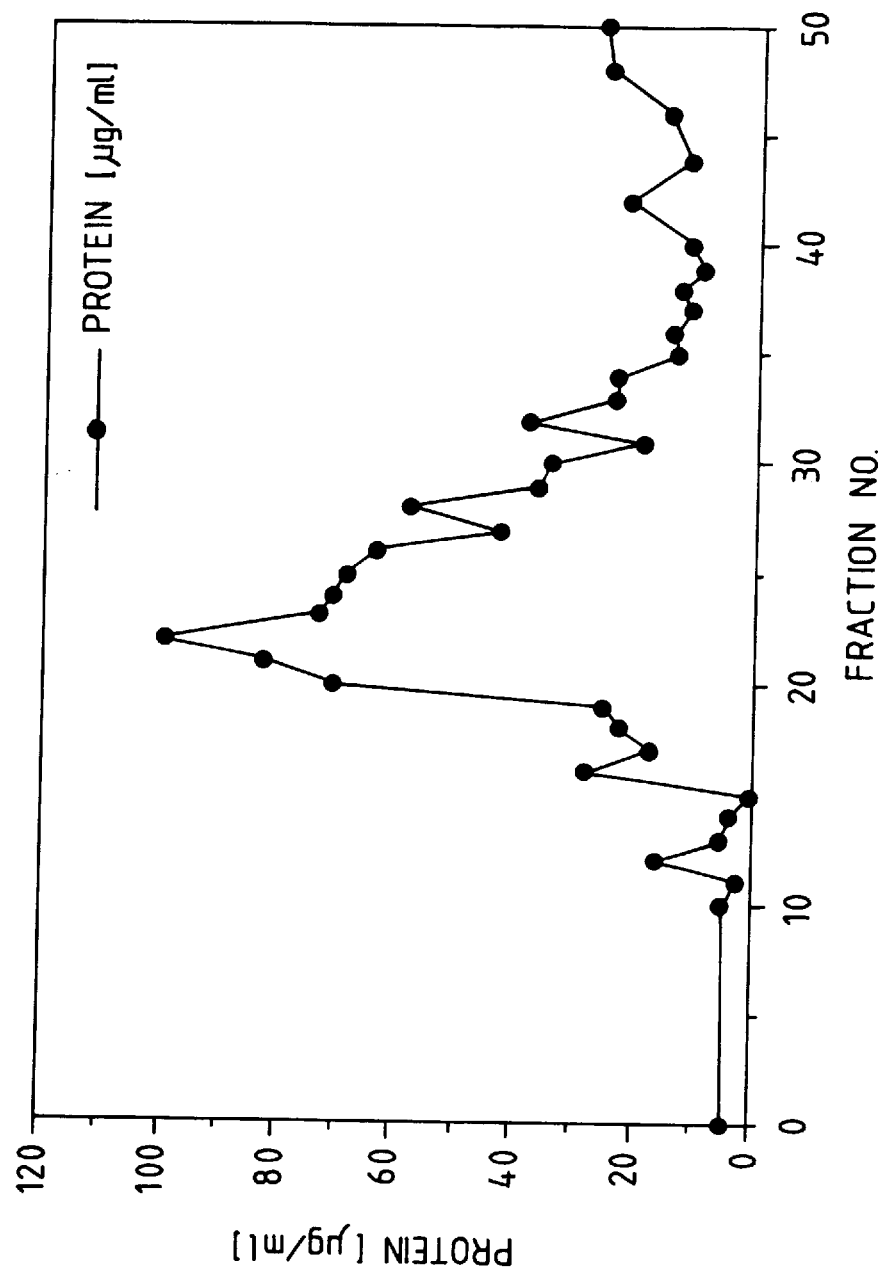
FIG. 2 illustrates a result of quantitative determination of protein in a phospholipid-protein coexisting system according to a conventional method.

The results of determination of protein are shown of each fractions are shown in FIG. 2.

The ruggedness of the elution curve in FIG. 2 is caused by error in the organic solvent extraction. On the contrary, in FIG. 1 illustrating the results of Example 11, such ruggedness is not found and measured values are on a smooth line. Accordingly, the method of the present invention is understood to be of high precision with little variation in comparison with conventional methods.

The present invention greatly simplifies determination of phospholipid which takes much labor conventionally. In particular the present invention provides an extremely simplified method for quantitative determination of lipid in a sample of lipid aggregate which is met in study of biomembrane containing lipid and in confirmation of composition of lipid-containing membrane synthesized artificially.

Furthermore, the present invention enables a simple and precise method of quantitative determination of two components such as a combination of lipid and protein, which could not be determined in a coexisting state owing to mutual interference, directly without laborious separation process like extraction.

What is claimed is:

1. A method of quantitative determination of lipid and protein, both of which coexist in a liquid sample, without separating either the lipid or the protein from the liquid sample, the lipid and the protein being capable of reacting with a color developing reagent to produce a reaction product which develops a color, comprising the steps of:

providing first standard liquid samples of the lipid, all of which have known concentrations, and using a first known process (a) to measure absorbances of the first standard liquid samples to obtain a relationship between the absorbances and the concentrations of the first standard liquid samples of the lipid, to calculate a first concentration constant (a1) of the lipid, providing first standard liquid samples of the protein, all of which have known concentrations, and using the process (a) to measure absorbances of the first standard liquid samples of the protein, to obtain a relationship between the absorbances and the concentrations of the first standard liquid samples of the protein, to calculate a first concentration constant (a2) of the protein, wherein said first known process (a) is capable of quantifying only said lipid or only said protein in said standard liquid samples;

providing second standard liquid samples of the lipid, all of which have known concentrations, and using a second known process (b) to measure absorbances of the second standard liquid samples, to obtain a relationship between the absorbances and the concentrations of the second standard liquid samples of the lipid to calculate a second concentration constant (b1) of the lipid;

providing second standard liquid samples of the protein, all of which have known concentrations, and using the process (b) to measure absorbances of the second standard liquid samples of the protein, to obtain a relationship between the absorbances and the concentrations of the second standard liquid samples of the protein to calculate a second concentration constant (b2) of the protein wherein said second known process (b) is capable of quantifying only said lipid or only said protein in said standard liquid samples;

providing the liquid sample containing the lipid and the protein whose concentrations are unknown, and using the processes (a) and (b) to measure absorbances (Va) and (Vb) of the liquid sample; and deriving actual concentrations of the lipid (x) and the protein (y) from the calculation of simultaneous equations (I) and (II)

$$Va = x \cdot a1 + y \cdot a2 \quad \text{(I)}$$

$$Vb = x \cdot b1 + y \cdot b2 \quad \text{(II)}$$

wherein the first known process (a) is different from the second known process (b), and process (b) is a Lowry method of a BCA (bicinchoninic acid) method and at least one of the processes (a) and (b) comprises the steps of reacting at least one of the lipid and protein in a sample with said color developing reagent to cause the sample containing the lipid and protein, to develop a color, and measuring the absorbances (Va) and (Vb) of said color-developed sample wherein each of the processes (a) and (b) is capable of quantifying the lipid and protein in said liquid sample.

2. A method according to claim 1, wherein the process (a) comprises measuring UV absorbance of the liquid samples, and the process (b) is the Lowry method.

3. A method according to claim 1, wherein the process (a) comprises measuring UV absorbance of the liquid samples, and the process (b) is the BCA method.

4. A method according to claim 1, wherein the process (a) is a Lowry method, and the process (b) is the BCA method.

5. A method according to claim 1, wherein the step for measuring the absorbances (Va) and (Vb) of the liquid sample comprises:

solubilizing the liquid sample with a surfactant to form a micelle composed of the lipid and the surfactant, and subsequently measuring the UV absorbance (Va) of the liquid sample, and measuring the absorbance (Vb) of the liquid sample by a process capable of detecting color development exhibited by the reaction between the color developing reagent and present in said liquid sample.

6. A method according to claim 5, wherein the process for measuring the absorbance (Vb) is a Lowry method.

7. A method according to claim 5, wherein the color developing reagent contains cupric ion and bicinchoninic acid.

8. A method according to claim 5, wherein the liquid sample a contains proteoliposome.

* * * * *

UNITED STATES PATENT AND TRADEMARK OFFICE
CERTIFICATE OF CORRECTION

PATENT NO. : 5,770,452

DATED : June 23, 1998

INVENTOR(S): NOBUKO YAMAMOTO ET AL.

Page 1 of 7

It is certified that error appears in the above-identified patent and that said Letters Patent is hereby corrected as shown below:

COLUMN 2

Line 16, "state" should read --states--;
Line 23, "have" should be deleted;
Line 55, "structure" should read --structures--.

COLUMN 3

Line 8, "Lowery" should read --Fowry--;
Line 26, "triptophan," should read --tryptophan,--;
Line 32, "triptophan" should read --tryptophan--.

COLUMN 4

Line 6, "two component" should read --two-component--;
Line 19, "a two" should read --a two---;
Line 38, "an" should read --a--;
Line 49, "b1" should read --$b_1$--.

COLUMN 6

Line 17, "Further" should read --Further,--.

COLUMN 9

Line 9, "completely" (second occurrence) should be deleted;
Line 21, "electronics" should read --Electronics--;
Line 39, "phopholipid" should read --phospholipid--.

UNITED STATES PATENT AND TRADEMARK OFFICE
CERTIFICATE OF CORRECTION

PATENT NO. : 5,770,452

DATED : June 23, 1998

INVENTOR(S): NOBUKO YAMAMOTO ET AL.

It is certified that error appears in the above-identified patent and that said Letters Patent is hereby corrected as shown below:

COLUMN 10

Line 8, "phopholipid" should read --phospholipid--;
Line 23, "the" should read --then--;
Line 53, "sample" should read --samples--;
Line 59, "an" should read --a--.

COLUMN 11

Line 23, "an" should read --a--;
Line 34, "10$\mu$g" should read --10$\mu$l--;
Line 46, "neither-lipid" should read --neither lipid--;
Line 50, "an" should read --a--.

COLUMN 12

Line 5, "an" should read --a--.

COLUMN 13

Line 17, "withn" should read --with--;
Line 28, "$0.310 = 3.03 \times 10^{-4}x + 2.99 \times 10^{-2}y$" should read
 --$0.310 = 3.03 \times 10^{-4}x + 2.99 \times 10^{-2}y$--;
Line 67, "an" should read --a--.

UNITED STATES PATENT AND TRADEMARK OFFICE
CERTIFICATE OF CORRECTION

PATENT NO. : 5,770,452

DATED : June 23, 1998

INVENTOR(S): NOBUKO YAMAMOTO ET AL.

It is certified that error appears in the above-identified patent and that said Letters Patent is hereby corrected as shown below:

COLUMN 14

Line 14, "20 $\mu$l 2.5 $\mu$l." should read --20 $\mu$l to 2.5 $\mu$l.--;
Line 48, "substraction" should read --subtraction--;
Line 49, "an" should read --a--;
Line 59, "forementioned" should read --aforementioned--;
Line 67, "substraction" should read --subtraction--.

COLUMN 15

Line 2, "an" should read --a--;
Line 7, "$B^P=9.63X10^{-2}Y$." should read --$B^P=9.63X10^{-2}y$.--;
Line 18, "protein;" should read --protein,--.

COLUMN 16

Line 17, "an" should read --a--;
Line 43, "an" should read --a--.

COLUMN 17

Line 3, "an" should read --a--;
Line 47, "bactrio-" should read --bacteriorhodopsin--;
Line 48, "thodpsin-" should be deleted;
Line 58, "minutes." should read --minute.--.

UNITED STATES PATENT AND TRADEMARK OFFICE
CERTIFICATE OF CORRECTION

PATENT NO. : 5,770,452          Page 4 of 7

DATED     : June 23, 1998

INVENTOR(S): NOBUKO YAMAMOTO ET AL.

It is certified that error appears in the above-identified patent and that said Letters Patent is hereby corrected as shown below:

COLUMN 18

Line 38, "bactrio-" should read --bacteriorhodopsin--;
Line 39, "thodpsin" should be deleted;
Line 48, "minutes." should read --minute.--.

COLUMN 19

Line 27, "came" should be deleted and "sample"
  should read --samples--;
Line 34, "an" should read --a--.

COLUMN 20

Line 22, "substraction" should read --subtraction--;
Line 23, "an" should read --a--;
Line 39, "substraction" should read --subtraction--;
Line 41, "an" should read --a--;
Line 58, "voltex" should read --vortex--.

COLUMN 22

Line 19, "sample," should read --samples,--;
Line 25, "an" should read --a--;
Line 63, "following" should read --the following--.

UNITED STATES PATENT AND TRADEMARK OFFICE
CERTIFICATE OF CORRECTION

PATENT NO. : 5,770,452

DATED : June 23, 1998

INVENTOR(S): NOBUKO YAMAMOTO ET AL.

It is certified that error appears in the above-identified patent and that said Letters Patent is hereby corrected as shown below:

COLUMN 23

Line 4, "in in" should read --in an--;
Line 7, "as" should read --an--;
Line 13, "mitochodria" should read --mitochondria--;
Line 15, "octylglcoside" should read --octylglycoside--.

COLUMN 24

Line 19, "an" should read --a--;
Line 32, "two fold)" should read --two-fold)--;
Line 60, "following" should read --the following--.

COLUMN 25

Line 15, "te" should read --the--;
Line 28, "(5)" should read --(6)--;
Line 50, "fractions" should read --fraction--;
Line 54, "minutes." should read --minute.--;
Line 65, "the each" should read --each of the--.

UNITED STATES PATENT AND TRADEMARK OFFICE
CERTIFICATE OF CORRECTION

PATENT NO. : 5,770,452

DATED : June 23, 1998

INVENTOR(S): NOBUKO YAMAMOTO ET AL.

It is certified that error appears in the above-identified patent and that said Letters Patent is hereby corrected as shown below:

COLUMN 26

Line 11, "of each" should read --for each--;
Line 12, "fractions are shown" should read --fraction--;
Line 31, "interfence" should read --interference--;
Line 45, "lipid," should read --lipid--;
Line 46, "lipid," should read --lipid;--;
Line 60, "samples," should read --samples--.

COLUMN 27

Line 22, "of" should read --or--;
Line 26, "protein," should read --protein--;
Line 29, "protein" should read --the protein--.

COLUMN 28

Line 20, "and present" should read --and the lipid and the protein present--;
Line 27, "a contains" should read --contains a--.

UNITED STATES PATENT AND TRADEMARK OFFICE
CERTIFICATE OF CORRECTION

PATENT NO. : 5,770,452
DATED : June 23, 1998
INVENTOR(S) : NOBUKO YAMAMOTO ET AL.

It is certified that error appears in the above-identified patent and that said Letters Patent is hereby corrected as shown below:

COLUMN 28

Line 20, "and present" should read --and the lipid and the protein present--;
Line 27, "a contains" should read --contains a--.

Signed and Sealed this

Fourth Day of May, 1999

Attest:

Q. TODD DICKINSON

Attesting Officer      Acting Commissioner of Patents and Trademarks